US009034978B2

(12) United States Patent
Thalappil et al.

(10) Patent No.: US 9,034,978 B2
(45) Date of Patent: May 19, 2015

(54) METHODS OF PREPARING METAL QUANTUM CLUSTERS IN MOLECULAR CONFINEMENT

(75) Inventors: Pradeep Thalappil, Chennai (IN); Udayabhaskararao Thumu, West Godavari Dist. (IN)

(73) Assignee: Indian Institute of Technology Madras, Chennai, Tamilnadu (IN)

( * ) Notice: Subject to any disclaimer, the term of this patent is extended or adjusted under 35 U.S.C. 154(b) by 115 days.

(21) Appl. No.: 13/807,971

(22) PCT Filed: Dec. 22, 2011

(86) PCT No.: PCT/IB2011/003105
§ 371 (c)(1),
(2), (4) Date: Jan. 2, 2013

(87) PCT Pub. No.: WO2013/061109
PCT Pub. Date: May 2, 2013

(65) Prior Publication Data
US 2014/0203213 A1 Jul. 24, 2014

(30) Foreign Application Priority Data

Oct. 28, 2011 (IN) .......................... 3692/CHE/2011

(51) Int. Cl.
| | | |
|---|---|---|
| C09K 11/00 | (2006.01) |
| C09K 11/02 | (2006.01) |
| B82Y 40/00 | (2011.01) |
| B82Y 20/00 | (2011.01) |
| C01B 17/20 | (2006.01) |
| C01B 19/00 | (2006.01) |
| C30B 7/00 | (2006.01) |
| C30B 29/02 | (2006.01) |
| G01N 33/543 | (2006.01) |
| H01L 29/12 | (2006.01) |
| B22F 9/18 | (2006.01) |
| B82Y 30/00 | (2011.01) |
| B22F 1/00 | (2006.01) |

(52) U.S. Cl.
CPC ............... *C09K 11/025* (2013.01); *B82Y 20/00* (2013.01); *B82Y 40/00* (2013.01); *B82Y 30/00* (2013.01); *Y10S 977/779* (2013.01); *Y10S 977/896* (2013.01); *Y10S 977/95* (2013.01); *C09K 11/00* (2013.01); *C01B 17/20* (2013.01); *C01B 19/007* (2013.01); *C30B 7/00* (2013.01); *C30B 29/02* (2013.01); *G01N 33/54393* (2013.01); *H01L 29/127* (2013.01); *B22F 1/0018* (2013.01); *B22F 9/18* (2013.01)

(58) Field of Classification Search
CPC .... C09K 11/025; C09K 11/02; Y10S 77/779; Y10S 977/896; Y10S 977/95; B82Y 40/00
USPC ......... 524/556; 252/310.36, 301.36; 977/779, 977/896, 950
See application file for complete search history.

(56) References Cited

U.S. PATENT DOCUMENTS

| | | | | |
|---|---|---|---|---|
| 2003/0129311 | A1* | 7/2003 | Huang ........................ | 427/337 |
| 2003/0148544 | A1* | 8/2003 | Nie et al. .................... | 436/524 |
| 2007/0161043 | A1 | 7/2007 | Nie et al. | |
| 2007/0269594 | A1 | 11/2007 | Ackerson et al. | |

FOREIGN PATENT DOCUMENTS

| | | |
|---|---|---|
| AU | 2002322348 A1 | 3/2003 |
| CA | 2450725 A1 | 1/2003 |
| CN | 102127428 A | 7/2011 |

(Continued)

OTHER PUBLICATIONS

International Search Report and Written Opinion for PCT/IB2011/003105 dated Mar. 19, 2012.
Adhikari et al., Facile Synthesis of Water-Soluble Fluorescent Silver Nanoclusters and $Hg^{II}$ Sensing, *Chem. Mater.* (Jul. 14, 2010) 22(15):4364-4371.
Bakr, et al., Silver Nanoparticles with Broad Multiband Linear Optical Absorption, *Angewandte Chemie* (Jul. 6, 2009) 121(32):6035-6040.

(Continued)

*Primary Examiner* — Michael M Bernshteyn
(74) *Attorney, Agent, or Firm* — Pepper Hamilton LLP

(57) ABSTRACT

Methods for the synthesis of metal quantum clusters within the framework of a porous gel matrix are described. For example, $Ag_{25}(glutathione)_{18}$ quantum clusters are synthesized in a cross-linked polyacrylamide gel matrix. The methods can be performed on large-scale and yields monodispersed metal quantum clusters.

17 Claims, 1 Drawing Sheet

(56) References Cited

FOREIGN PATENT DOCUMENTS

| EP | 1410031 A2 | 4/2004 |
|---|---|---|
| JP | 2005508493 A | 3/2005 |
| WO | WO 03/003015 A2 | 1/2003 |
| WO | WO2008/054471 A2 | 5/2008 |

OTHER PUBLICATIONS

Cathcart et al., Silver Nanoclusters: Single-Stage Scaleable Synthesis of Monodisperse Species and Their Chirooptical Properties, *J. Phys. Chem. C* (Jun. 14, 2010), 114(38):16010-16017.

Haynes et al., Nanoparticle Optics: The Importance of Radiative Dipole Coupling in Two-Dimensional Nanoparticle Arrays, *J. Phys. Chem. B* (May 1, 2003), 107:7337-7342.

Jin, Quantum sized, thiolate-protected gold nanoclusters, *Nanoscale* (Dec. 8, 2009), 2(3):343-362.

Kumar et al., Glutathione-Stabilized Magic-Number Silver Cluster Compounds, *J. Am. Chem. Soc.* (Sep. 7, 2010), 132(38):113141-13143.

Love et al. Synthesis of gold nanoparticles within a supramolecular gel-phase network, *Chemical Communications* (Feb. 22, 2005), 15:1971-1973.

Negishi et al., Glutathione-protected gold clusters revisited: bridging the gap between gold[1]-thiolate c, *J. Am. Chem. Soc.* (Dec. 9, 2010), 127:5261-5270.

Petty et al., DNA-Templated Ag Nanocluster Formation, *J. Am. Chem. Soc.* (Apr. 2, 2004), 126(16):5207-5212.

Peyser et al, Photoactivated fluorescence from individual silver nanoclusters, *Science* (Jan. 5, 2001) 291:103-106.

Rao et al., $Ag_9$ quantum cluster through a solid state route, *J. Am. Chem. Soc.* (2010), 132(46):16304-16307.

Rao et al. Luminescent $Ag_7$ and $Ag_8$ Clusters by Interfacial Synthesis, *Angewandte Chemie* (2010) 49:3925-3929.

Saravanan et al., A study on synthesis and properties of Ag nanoparticles immobilized polyacrylamide hydrogel composites, *Materials Chemistry and Physics* (Jun. 15, 2007), 103(2-3):278-282.

Shang et al., Facile preparation of water-soluble fluorescent silver nanoclusters using a polyelectrolyte template, *Chemical Communications* (Jan. 10, 2008), 9:1088-1090.

Shen et al., Water-Soluble Fluorescent Ag Nanoclusters Obtained from Multiarm Star Poly(acrylic acid) as Molecular Hydrogel Templates, *Advanced Materials* (Jan. 29, 2007), 19(3):349-352.

Shibu et al., Ligand Exchange of $Au_{25}SG_{18}$ Leading to Functionalized Gold Clusters: Spectroscopy, Kinetics, and Luminescenc, *J. Phys. Chem. C* (Jul. 17, 2008), 112(32),12168-12176.

Sivaramakrishnan et al., Controlled insulator-to-metal transformation in printable polymer composites with nanometal clusters, *Nat. Mater.* (Feb. 2007), 6(2):149-155.

Wu et al., High Yield, Large Scale Synthesis of Thiolate-Protected $Ag_7$ Clusters, *J. Am. Chem. Soc.* (Nov. 3, 2009), 131(46):16672-16674.

Wu et al., One-Pot Synthesis of Au25(SG)18 2- and 4-NM Gold Nanoparticles and Comparison of Their Size-Dependent Properties, *Advanced Functional Materials* (Oct. 19, 2010), 21(1):177-183.

Xu et al., Water-Soluble Fluorescent Silver Nanoclusters, *Advanced Materials* (2010) 22:1078-1082.

Zheng et al., Individual Water-Soluble Dendrimer-Encapsulated Silver Nanodot Fluorescence, *J. Am. Chem. Soc.* (Oct. 31, 2002), 124(47):13982-13983.

Zhu et al., Atomically precise $Au_{25}(SR)_{18}$ nanoparticles as catalysts for the selective hydrogenation of α, β-unsaturated ketones and aldehydes, *Angewandte Chemie* (Jan. 14, 2010), 122(7):1317-1320.

* cited by examiner

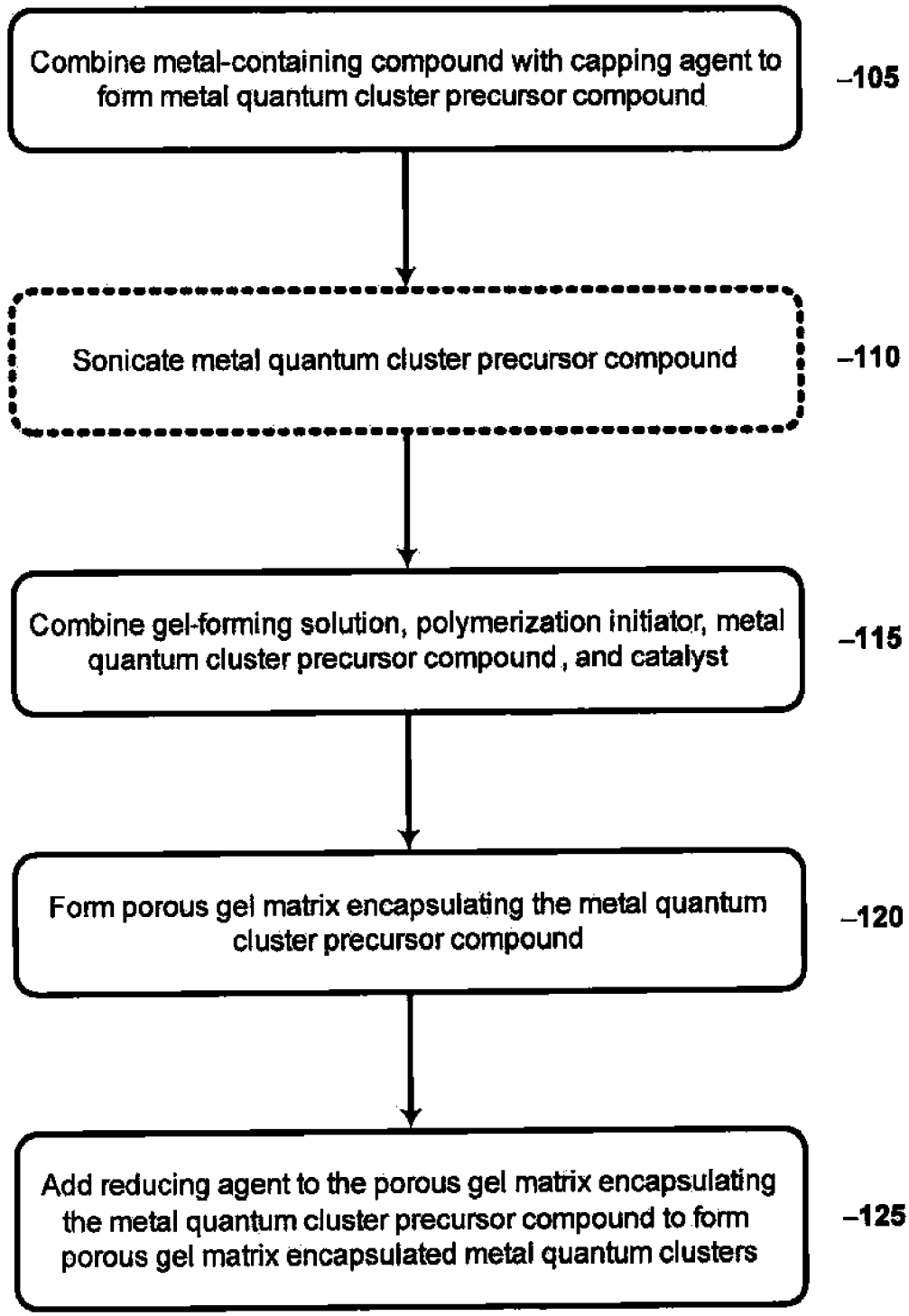

METHODS OF PREPARING METAL QUANTUM CLUSTERS IN MOLECULAR CONFINEMENT

CLAIM OF PRIORITY

This application is a U.S. national stage filing under 35 U.S.C. §371 of International Application No. PCT/IB2011/003105, filed Dec. 22, 2011 and entitled "Methods Of Preparing Metal Quantum Clusters In Molecular Confinement," and also claims the benefit of the Indian Application No. 3692/CHE/2011, filed Oct. 28, 2011, the disclosure of which is incorporated by reference.

BACKGROUND

Metal quantum clusters (MQCs) have fascinating size-dependent properties including discrete electronic energy levels and 'molecule-like' optical transitions in their absorption and emission spectra. As such, MQCs can be used for single molecule optics, nanophotonics, bioscience, catalysis, and other similar applications. The practical use of MQCs in such applications will require the large-scale synthesis of monodisperse MQCs.

Conventional methods for the synthesis of MQCs are based on solution-phase routes. Typically, MQCs of various sizes are made together in a synthetic procedure. In order to get monodispersed MQCs with well-defined molecular formulae, size-separation using elaborate chromatographic techniques is required.

SUMMARY

This disclosure is not limited to the particular systems, devices and methods described, as these may vary. The terminology used in the description is for the purpose of describing the particular versions or embodiments only, and is not intended to limit the scope.

Methods of growing metal quantum clusters within a porous gel matrix are described herein. These methods allow for the large-scale synthesis of monodispersed metal quantum clusters using a single-step approach, which may improve the availability and utility of metal quantum clusters. By growing metal quantum clusters within a porous gel matrix, monodisperse uniform nanoparticles may be produced more easily and/or in better yields than in free-solution approaches. It is believed that the growth of the metal quantum clusters is encouraged within but limited by the size of the pores of the gel matrix. Because individual cluster growth is determined by pore size a monodisperse and uniform population is readily made.

In an embodiment, a method of synthesizing metal quantum clusters includes growing the metal quantum clusters in a porous gel matrix. This embodiment includes formation of a porous gel matrix that encapsulates a metal quantum cluster precursor compound and the introduction of a reducing agent to form the metal quantum clusters.

In an embodiment, a method of synthesizing metal quantum clusters includes forming a porous gel matrix from the mixture comprising a metal-containing compound, a capping agent, and a gel-forming solution and adding a reducing agent to form the metal quantum clusters.

In an embodiment, a kit for synthesizing metal quantum clusters includes a metal-containing compound, a capping agent, a gel-forming solution, a reducing agent, and instructions for use.

In an embodiment, a gel matrix includes a porous gel encapsulating a metal quantum cluster precursor compound.

In an embodiment, a gel matrix includes a porous gel encapsulating metal quantum clusters of the formula $Ag_{18}$(glutathione)$_{25}$.

BRIEF DESCRIPTION OF THE DRAWINGS

FIG. 1 is a flowchart that illustrates an exemplary method for synthesizing metal quantum clusters, in accordance with an embodiment.

DETAILED DESCRIPTION

Methods of growing metal quantum clusters within a porous gel matrix are described herein. These methods allow for the large-scale synthesis of monodispersed metal quantum clusters using a single-step approach, which may improve the availability and utility of metal quantum clusters.

In an embodiment, metal quantum clusters are grown within a porous gel matrix. Despite variations in nomenclature concerning small-sized particles based on size regimes, properties, and makeup, the term metal quantum clusters is not intended to be limiting, but instead refer to particular products of the general methods described herein.

The average diameter of metal quantum clusters may be less than about 5 µm, or about 100 nm to about 0.5 nm, or about 10 nm to about 1 nm. Specific examples of average diameters include about 5 µm, about 400 nm, about 300 nm, about 200 nm, about 100 nm, about 50 nm, about 40 nm, about 30 nm, about 20 nm, about 10 nm, about 1 nm, about 0.5 nm, and ranges between any two of these values. The standard deviation of the diameter of the metal quantum clusters may be less than or equal to about 15% of the average diameter, less than or equal to about 10% of the average diameter, less than or equal to about 5% of the average diameter, or the metal quantum clusters may be monodisperse.

Materials for making metal quantum clusters are well-known to a person having ordinary skill in the art, and the examples described herein are not intended to be limiting. The metal quantum clusters may comprise Mg, Zn, Fe, Cu, Sn, Ti, Ag, Au, Cd, Se, Si, Pt, S, Ni or combinations thereof. For example, the metal quantum clusters may be of the formula $Ag_{25}$(glutathione)$_{18}$.

FIG. 1 is a flow diagram describing a method for synthesizing metal quantum clusters within a porous gel matrix according to an embodiment. As shown in FIG. 1, a metal containing compound and a capping agent may be combined 105 to form a metal quantum cluster precursor compound.

The metal-containing compound used to make the metal quantum clusters may be a metal thioate, an organometallic compound, a metal oxide, an inorganic salt, a coordination compound, or a combination thereof. In an embodiment, the metal-containing compound used to make the metal quantum clusters may contain Mg, Zn, Fe, Cu, Sn, Ti, Ag, Au, Cd, Se, Si, Pt, S, Ni or a combination thereof. For example, the metal-containing compound used to make the metal quantum clusters may be $AgNO_3$.

The surface of the metal quantum clusters may comprise at least one layer of capping agents. The capping agent may be used to control the growth, improve the solubility, provide chemical functionality, or otherwise alter the properties the metal quantum clusters. Materials used as capping agents are well-known to a person having ordinary skill in the art, and the examples described herein are not intended to be limiting. Despite variations in nomenclature regarding surface-functionalization of metals based on chemical makeup and properties, the term capping agent is not intended to be limiting, but instead refers to particular products of the general methods described herein. The capping agent can comprise an aromatic group, a conjugated pi system, a pi bond, a nitrogen atom, an oxygen atom, a sulphur atom, a phosphorus atom, an aromatic thiol or an aliphatic thiol. In an embodiment, the capping agent may be an organosulfur compound. For example, the capping agent may be a thiol. As a specific example, the capping agent may be glutathione thiolate.

The metal quantum cluster precursor compound is the starting material used in the formation of the metal quantum clusters. The metal quantum cluster precursor compound may be a metal-containing compound, or the metal quantum cluster precursor compound may be formed by mixing a metal-containing compound with a capping agent. The metal quantum cluster precursor compound may optionally be sonicated 110. Aggregates may sometimes be present in the metal quantum cluster precursor compound. Any unwanted aggregates may be dispersed by sonicating 110 the metal quantum cluster precursor compound.

A mixture may be formed 115 by combining a gel-forming solution, a polymerization agent, and a metal quantum cluster precursor compound. The gel-forming solution is a liquid comprising the materials used to form a porous gel matrix. In an embodiment, the gel-forming solution may be a polymer or a polymerizable material. For example, the polymerizable material may be acrylamide, bisacrylamide, piperazine diacrylamide, diallyltartardiamide, dihydroxyethylene-bis-acrylamide, bis-acrylylcystamine or mixtures thereof. Typical mixtures of the polymerizable material may comprise acrylamide and at least one cross-linker selected from bisacrylamide, piperazine di-acrylamide, diallyltartardiamide, dihydroxyethylene-bis-acrylamide, and bis-acrylylcystamine. In some examples, the polymerizable material may be a mixture of acrylamide and the cross-linker bisacrylamide.

A gel-forming solution may use a change in temperature, additional reagents, or both a change in temperature and additional reagents to form a porous gel matrix. The additional reagents may be polymerization agents such as catalysts and polymerization initiators and combinations thereof. For example, polymerization agents may be N,N,N',N'-tetramethyl-ethane-1,2-diamine (TMED), ammonium persulfate, riboflavin-5'-phosphate, or mixtures thereof.

The mixture of the gel-forming solution, a polymerization agent, and a metal quantum cluster precursor compound may polymerize and allow formation 120 of the porous gel matrix encapsulating the metal quantum cluster precursor compound. In an embodiment, porous gel matrix matrices are composed of molecular cages which may be used to control mass transfer of reagents and nucleate the preferred metal quantum clusters. Metal quantum clusters grown using this method, may be at least partially encapsulated by the porous gel matrix.

The materials and methods for making porous gel matrix matrices are well-known to a person having ordinary skill in the art, and the examples described herein are not intended to be limiting. The porous gel matrix may comprise a sol-gel or a polymer. In an embodiment, the porous gel matrix may comprise agarose or cross-linked polyacrylamide. For example, the porous gel matrix may comprise a polyacrylamide cross-linked with bisacrylamide, agarose gel, cellulose gel, or a starch gel.

Methods that vary the pore size of the porous gel matrix may alter the diameter of the metal quantum clusters grown within the porous gel matrix. In some embodiments, increasing the cross-linker concentration in the gel-forming solution may induce a systematic increase in the pore size of the porous gel matrix and may facilitate the growth of larger metal quantum clusters within the matrix. The following table is exemplary only, it is not meant to limit the invention in any way.

| Exemplary Gel formulation | Resultant pore size (average) | Resultant cluster size (average) | Resultant cluster |
|---|---|---|---|
| 53% Acrylamide monomer; 14.5% bisacrylamide crosslinker | 2-30 μm | about 10 nm to about 1 nm | nanoparticles |
| 51% Acrylamide monomer; 7.8% bisacrylamide crosslinker (Example 1) | 2-10 μm | <1 nm | >80% $Ag_{25}(glutathione)_{18}$ |

Using the methods described herein, a porous gel matrix made using a gel-forming solution can be made to have desired pore sizes, resulting in a desired quantum cluster of a desired size, wherein the resultant quantum clusters are substantially all the desired quantum cluster and substantially free of polydisperse plasmonic nanoparticles. Preferably the content of the desired metal quantum clusters is greater than about 80%, greater than about 90%, greater than about 95%, greater than about 97%, greater than about 99%, greater than about 99.5%, or greater than about 99.9% of all the metal quantum clusters formed. For example, a porous gel matrix comprising 51% acrylamide monomer and 7.8% bisacrylamide crosslinker yields a matrix comprising metal quantum clusters that are substantially all $Ag_{25}(glutathione)_{18}$ metal quantum clusters. Preferably the content of $Ag_{25}(glutathione)_{18}$ metal quantum clusters is greater than about 80%, greater than about 90%, greater than about 95%, greater than about 97%, greater than about 99%, greater than about 99.5%, or greater than about 99.9% of all the metal quantum clusters formed.

Monodispersity of a metal quantum cluster sample may be confirmed by UV-Vis spectroscopy, polyacrylamide gel electrophoresis and electrospray ionisation mass spectrometry. A sample of monodisperse metal quantum clusters may show strong quantum size effects such as multiple molecule-like transitions in the optical absorption spectrum, whereas metal nanoparticles may show a dominant plasmon resonance band. In an embodiment, the UV-Vis spectrum of an aqueous solution of $Ag_{25}(glutathione)_{18}$ metal quantum clusters shows prominent features at about 350, 480, and 650 nm indicating that the clusters obtained were monodispersed. Further confirmation of monodispersity in a metal quantum cluster sample can be had via gel electrophoresis, where elution of a single band may indicate that only one type of cluster is present. In an embodiment, a sample of $Ag_{25}(glutathione)_{18}$ metal quantum clusters produced a single band when subjected to polyacrylamide gel electrophoresis. Finally, a mass spectrum of monodisperse metal quantum clusters may be substantially free of all features not corresponding to the ionized metal quantum cluster and its multiply charged ions that originate from ligand deprotonation. In an embodiment, the electrospray ionization mass spectrum of $Ag_{25}(glutathione)_{18}$ taken in negative ion mode showed only the parent peak of $[Ag_{25}(glutathione)_{18}]^-$ at m/z=1641.1 and peaks from a series of multiply charge ions originating from deprotonation of the 18 glutathione ligands.

In an embodiment, the porous gel matrix may encapsulate the metal quantum cluster precursor compound. The metal quantum cluster precursor compound may be introduced to the porous gel matrix by adding the metal quantum cluster precursor compound to the gel-forming solution, by adding the metal quantum cluster precursor compound to the porous gel matrix, or by forming the metal quantum cluster precursor compound within the porous gel matrix.

Referring back to FIG. 1, a reducing agent may be added 125 to the porous gel matrix encapsulating the metal quantum cluster precursor. The reducing agent may be used to form metal quantum clusters within the porous gel matrix through the reduction of the metal quantum cluster precursor compound. Materials used as reducing agents are well-known to a person having ordinary skill in the art, and the examples described herein are not intended to be limiting. The reducing agent may be an inorganic salt. In some embodiments, the reducing agent may be $NaBH_4$, $LiAlH_4$, nascent hydrogen, borane-tetrahydrofuran complex, or sodiumcyanoborohydride.

The reducing agent may be introduced to the porous gel matrix by adding the reducing agent to the gel-forming solution, by passive permeation of the reducing agent into the porous gel matrix, or by using an applied current to carry the reducing agent through the porous gel matrix.

In an embodiment, formation of the preferred metal quantum clusters can include lowering the reaction temperature between the reducing agent and the metal quantum cluster precursor compound. For example, the reducing agent and the porous gel matrix encapsulating the metal quantum cluster precursor compound may be cooled below room temperature prior to introducing the reducing agent to the porous gel matrix. In some embodiments, they are cooled to about 20° C. or below, about 15° C. or below, about 10° C. or below, about 5° C. or below, or to about 0° C. or to a range between any two of these values. In particular, the reducing agent and the porous gel matrix encapsulating the metal quantum cluster precursor compound may be cooled to about 0° C. prior to introducing the reducing agent to the porous gel matrix.

Following formation of the metal quantum clusters, the reaction may be stopped by removing excess reducing agent from the porous gel matrix. Solvent extraction may be used to remove excess reducing agent. The extraction solvent may be an alcohol, such as ethanol or methanol.

Further use of the metal quantum clusters may include separation or isolation of the metal quantum clusters from the porous gel matrix. Pulverizing the porous gel matrix may improve the isolation of the metal quantum clusters from the porous gel matrix.

In some embodiments, solvent extraction may be used to extract metal quantum clusters from the porous gel matrix. The extraction solvent may be aqueous. For example, the extraction solvent may be water, water and about 20% methanol, water and about 20% tetrahydrofuran, or water and about 20% dimethylformamide. Centrifugation may be used to separate insoluble gel fragments from a solution containing metal quantum clusters. Purification of dissolved metal quantum clusters may be achieved by precipitating the metal quantum clusters. In an embodiment, addition of a solvent may be used to precipitate the metal quantum clusters from an aqueous solution. The precipitation solvent may be an alcohol such as ethanol or methanol, or it may be an organic solvent such as acetone or acetonitrile.

In other embodiments, the porous gel matrix may be dissolved with a suitable solvent. The metal quantum clusters may dissolve with the porous gel matrix, or may remain insoluble. In embodiments where the metal quantum clusters are not dissolved along with the porous gel matrix, centrifugation may be used to separate the insoluble metal quantum clusters from the solution. In embodiments where the metal quantum clusters are dissolved along with the porous gel matrix, selective precipitation may be used to isolate the metal quantum clusters.

Removal of solvent may be used to acquire a dry powder of metal quantum clusters. Solvent may be removed by applying a vacuum, raising the temperature, decanting, or any combination thereof. For example, solvent may be removed by applying a vacuum at elevated temperature. The isolated yield of metal quantum clusters may be about 30% to about 100%, about 50% to about 80%, about 66%, or about 63%, based on the weight of the metal-containing compound. Specific examples of yield include about 30%, about 40%, about 50%, about 60%, about 70%, about 80%, about 90%, about 95%, about 99%, and ranges between any two of these values. In an ideal example, the yield is about 100% or is 100%.

A phase-transfer reagent may be used to alter the solubility properties of the metal quantum clusters. Water soluble metal quantum clusters may be transferred to an organic solvent by dissolving the metal quantum clusters in an aqueous solvent and adding a phase-transfer reagent dissolved in an organic solvent. The mixture of metal quantum clusters and phase-transfer reagent may be heated, stirred, or heated and stirred. Suitable phase-transfer reagents include but are not limited to quaternary ammonium cations, such as benzyltrimethylammonium chloride or tetraoctylammonium bromide, and phosphonium salts, such as tetraphenylphosphonium chloride. The phase-transfer reagent may be tetraoctylammonium bromide. The organic solvent may be immiscible with water. For example, suitable solvents include organic solvents, such as toluene, dichloromethane, carbontetrachloride, hexane, cyclohexane, pentane, and diethyl ether.

The aqueous and organic solvents may be separated. Ethanol, for example, may be added to the organic layer to precipitate the phase-transferred metal quantum clusters. The precipitated phase-transferred metal quantum clusters may be washed, isolated, dried, or any combination thereof. The precipitated phase-transferred metal quantum clusters may be redispersible in an organic solvent. The phase-transferred metal quantum clusters may be more stable when compared to the metal quantum clusters in an aqueous solution.

In an embodiment, a kit for making metal quantum clusters may be provided. The kit may comprise: a metal-containing compound, a capping agent, a gel-forming solution, a reducing agent, and instructions for preparing the metal quantum clusters. In an embodiment, the kit may include four containers, wherein: the metal-containing compound is in the first container, the capping agent is in the second container, the gel-forming solution is in the third container, and the reducing agent is in the fourth container.

The metal-containing compound provided in the kit may be a metal thiolate, an organometallic compound, a metal oxide, an inorganic salt, a coordination compound, or a combination thereof. In an embodiment, the metal-containing compound provided in the kit may contain Mg, Zn, Fe, Cu, Sn, Ti, Ag, Au, Cd, Se, Si, Pt, S, Ni or a combination thereof. For example, the metal-containing compound provided in the kit may be $AgNO_3$.

The capping agent provided in the kit can comprise an aromatic group, a conjugated pi system, a pi bond, a nitrogen atom, an oxygen atom, a sulphur atom or a phosphorus atom. In an embodiment, the capping agent provided in the kit may be an organosulfur compound. For example, the capping agent provided in the kit may be a thiol. In particular, the capping agent provided in the kit may be glutathione thiolate.

The gel-forming solution provided in the kit is a liquid comprising the materials used to form a porous gel matrix. In an embodiment, the gel-forming solution provided in the kit may be a polymer or a polymerizable material. For example, the polymerizable material provided in the kit may be acrylamide, bisacrylamide, piperazine di-acrylamide, diallyltartardiamide, dihydroxyethylene-bis-acrylamide, bis-acrylylcystamine or mixtures thereof. In particular, the polymerizable material provided in the kit may be a mixture acrylamide and bisacrylamide.

The gel-forming solution provided in the kit may use a change in temperature, additional reagents, or both a change in temperature and additional reagents to form a porous gel matrix. The additional reagents may be polymerization agents such as catalysts and polymerization initiators and may be included in the kit. In an embodiment two additional containers with the polymerization agents N,N,N',N'-tetramethyl-ethane-1,2-diamine (TMED) and ammonium persulfate are provided in the kit. As will be appreciated by those skilled in the art, the polymerization agents should be separate from the polymerizable material until polymerization is desired.

The reducing agent provided in the kit may be an inorganic salt. For example, the reducing agent may be $NaBH_4$.

The solubility of the metal quantum clusters made using the kit can optionally be changed from organic to aqueous or from aqueous to organic. In an embodiment, the kit will provide an additional container with a phase-transfer agent. The phase-transfer reagent may be tetraoctylammonium bromide.

Embodiments illustrating the method and materials used may be further understood by reference to the following non-limiting examples.

EXAMPLES

Example 1

Preparation of Metal Quantum Clusters in a Porous Gel

The metal quantum cluster precursor compound was formed by dissolving $AgNO_3$ (47 mg, 276 mM) and glutathione (GSH) (150 mg, 489 mM) in a 1 mL solution of NaOH (60 mg, 1.5 mM, triply distilled water) at room temperature. The solution was vigorously stirred and sonicated to make a uniform solution of Ag(I)thiolate.

The gel-forming solution was formed by mixing acrylamide(T)/bisacrylamide(C) (51% T, 7.8% C) and 20 μL of 0.1% ammonium persulfate in a 250 mL beaker. 0.7 mL of the metal quantum cluster precursor solution was added and stirred. With the addition of 10 μL N,N,N',N'-tetramethyl-ethane-1,2-diamine (TMED), polymerization leading to the porous gel matrix occurred. The gel was cooled to 0° C.

Formation of the metal quantum clusters was initiated by adding ice cold, aq. $NaBH_4$ (0.5 M, 10 mL) on top of the porous gel matrix encapsulating metal quantum cluster precursor. The color of the gel changed from light yellow to dark brown within half an hour indicating the formation of gel-encapsulated metal quantum clusters.

Example 2

Isolation of Metal Quantum Clusters from a Porous Gel Matrix

The porous gel matrix was pulverized, and the metal quantum clusters were extracted into water. This aqueous solution of metal quantum clusters was centrifuged at 15,000 rpm to remove traces of the porous gel matrix. Excess ethanol was added to precipitate the metal quantum clusters. Removal of solvent under reduced pressure led to a dry powder of metal quantum clusters.

Example 3

Phase Transfer of Metal Quantum Clusters

An aqueous solution of metal quantum clusters (5 mg/mL) was mixed with 5 mM tetraoctylammonium bromide (TOABr) in toluene and stirred vigorously for 2 minutes. Metal quantum clusters underwent immediate and complete phase transfer from the aqueous to the toluene layer. The phase transfer was monitored visually by color changes in the aqueous and toluene layers. The colorless toluene layer turned reddish brown and the aqueous layer, which was originally reddish brown, turned colorless after stirring. Ethanol was added to the toluene layer to precipitate the phase transferred metal quantum clusters. The precipitate was washed two times with ethanol, centrifuged and dried. This powder was redispersible in toluene.

Example 4

Determining Product Monodispersity and Composition

The UV-Vis spectrum of an aqueous solution of the product from Example 2 shows prominent features at 330, 478, and 640 nm, and is devoid of a plasmon resonance band. These multiple molecule-like transitions in the optical absorption spectrum are indicative of a sample containing monodisperse metal quantum clusters.

Polyacrylamide gel electrophoresis gels were made with a 1 mm thick spacer where the total contents of the acrylamide monomers were 28% (bis(acrylamide:acrylamide)=7:93) and 3% (bis(acrylamide:acrylamide)=6:94) for the separation and condensation gels, respectively. The eluting buffer consisted of 192 mM glycine and 25 mM tris(hydroxymethylamine). The crude mixture of metal quantum clusters, as a reddish brown powder, obtained in the reaction from example 2 was dissolved in 5% (v/v) glycerol-water solution (1.0 mL) at a concentration of 60 mg/mL. The sample solution (1.0 mL) was loaded onto a 1 mm gel and eluted for 4 h at a constant voltage of 150 V to achieve separation. The metal quantum clusters appeared as a single band in the gel, further indicating that the sample was contained monodisperse metal quantum clusters.

Electrospray ionization mass spectrometry was performed on the product from example 3 in methylene chloride. The spectrum taken in negative ion mode showed only the parent peak of $[Ag_{25}(glutathione)_{18}]^-$ at m/z=1641.1 and peaks from a series of multiply charge ions originating from deprotonation of the 18 glutathione ligands. The absence of other features and the mass correlation to the desired metal quantum clusters confirms that the synthesized product is $Ag_{25}$(glutathione)$_{18}$ metal quantum clusters.

Example 5

Preparation of Nanoparticles

Silver nitrate ($AgNO_3$, 47 mg, 276 mM) and glutathione (GSH) (150 mg, 489 mM) will be dissolved in a 1 mL solution of NaOH (60 mg, 1.5 mM, triply distilled water) at room temperature. The solution will be vigorously stirred and sonicated to make a uniform solution of Ag(I)thiolate. Formation of the nanoparticles will be initiated by adding ice cold, aq. NaBH$_4$ (0.5 M, 10 mL) to the solution of Ag(I)thiolate. Polydisperse plasmonic nanoparticles will be isolated by centrifugation, removal of supernatant, dispersion of the resulting pellet in water, and a second centrifugation and removal of supernatant step.

In the present disclosure, reference is made to the accompanying figure, which form a part hereof. The illustrative embodiments described in the detailed description, figure, and claims are not meant to be limiting. Other embodiments may be used, and other changes may be made, without departing from the spirit or scope of the subject matter presented herein. It will be readily understood that the aspects of the present disclosure, as generally described herein, and illustrated in the figure, may be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or figure, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 substituents refers to groups having 1, 2, or 3 substituents. Similarly, a group having 1-5 substituents refers to groups having 1, 2, 3, 4, or 5 substituents, and so forth.

What is claimed is:

1. A method of making metal quantum clusters, the method comprising:
   mixing at least one metal quantum cluster precursor compound with at least one polymerizable material to form a mixture;
   combining the mixture with at least one polymerization agent to form the porous gel matrix which encapsulates the metal quantum cluster precursor compound; and
   growing metal quantum clusters within a porous gel matrix,
   wherein the forming of the porous gel matrix and the growing of the metal quantum clusters is a single-step.

2. The method of claim 1, wherein the at least one metal quantum cluster precursor compound is prepared by reacting a metal-containing compound with a capping agent to yield the metal quantum cluster precursor compound.

3. The method of claim 2, wherein the mixing at least one metal-containing compound comprises mixing at least metal containing compound selected from the group consisting of: metal thiolates, organometallic compounds, metal oxides, inorganic salts, coordination compounds, and combinations thereof.

4. The method of claim 2, wherein the mixing at least one metal-containing compound comprises mixing at least one metal containing compound selected from the group consisting of: Mg, Zn, Fe, Cu, Sn, Ti, Ag, Au, Cd, Se, Si, Pt, S, Ni or combinations thereof.

5. The method of claim 2, wherein reacting the at least one metal containing compound with a capping, comprises reacting the metal containing compound an aromatic group, a conjugated pi system, a pi bond, a nitrogen atom, an oxygen atom, a sulphur atom, a phosphorus atom, an aromatic thiol, an aliphatic thiol, or combinations thereof.

6. The method of claim 2, wherein reacting the at least one metal containing compound with a capping agent, comprise reacting the metal containing compound with an organosulfur compound.

7. The method of claim 2, wherein the reacting at least one metal containing compound with a capping agent yields a metal precursor that is a metal thiolate.

8. The method of claim 1, wherein mixing the at least one metal quantum cluster precursor compound with at least one polmerizable material, comprises mixing the at least one metal quantum cluster precursor compound with acrylamide, bisacrylamide, piperazine di-acrylamide, diallyltartardiamide, dihydroxyethylene-bis-acrylamide, bis-acrylylcystamine or mixtures thereof.

9. The method of claim 1, further comprising mixing the porous gel matrix with a reducing agent to reduce the metal quantum cluster precursor compound to the metal quantum cluster.

10. The method of claim 9, wherein mixing the porous gel matrix with a reducing agent, comprises mixing the porous gel matrix with an inorganic salt.

11. The method of claim 1, wherein the average diameter of the metal quantum clusters is smaller than about 5 μm.

12. The method of claim 1, wherein the average diameter of the metal quantum clusters is about 100 nm to about 0.5 nm.

13. The method of claim 1, wherein the diameter of the metal quantum clusters is monodisperse.

14. The method of claim 1, further comprising isolating the metal quantum clusters from the porous gel matrix.

15. The method of claim 14, further comprising purifying the metal quantum clusters.

16. The method of claim 14, further comprising precipitating the metal quantum clusters by addition of a solvent after the isolating step.

17. The method of claim 1, further comprising:
dissolving the metal quantum clusters in water; and
adding a phase-transfer reagent dissolved in an organic solvent, whereby the metal quantum clusters are transferred to the organic phase.

* * * * *